US00PP27681P3

(12) United States Plant Patent
Sills et al.

(10) Patent No.: US PP27,681 P3
(45) Date of Patent: Feb. 21, 2017

(54) BLACKBERRY PLANT NAMED 'DRISBLACKTHIRTEEN'

(50) Latin Name: ***Rubus* L. subgenus *Rubus***
Varietal Denomination: DrisBlackThirteen

(71) Applicant: Driscoll's, Inc., Watsonville, CA (US)

(72) Inventors: Gavin R. Sills, Gilroy, CA (US); Andrea M. Pabon, Gilroy, CA (US); Mark Crusha, Capitola, CA (US)

(73) Assignee: Driscoll's, Inc., Watsonville, CA (US)

( * ) Notice: Subject to any disclaimer, the term of this patent is extended or adjusted under 35 U.S.C. 154(b) by 48 days.

(21) Appl. No.: 14/544,298

(22) Filed: Dec. 19, 2014

(65) Prior Publication Data

US 2016/0183424 P1 Jun. 23, 2016

(51) Int. Cl.
*A01H 5/08* (2006.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| 2016/0183425 | P1 | 6/2016 | Sills et al. |
| 2016/0249505 | P1 | 8/2016 | Sills et al. |

OTHER PUBLICATIONS

Sills et al., U.S. Appl. No. 14/999,063, filed Mar. 25, 2016, titled "Blackberry plant named DrisBlackSixteen".

Voss, Donald, "The Royal Horticultural Society Colour Chart 2001", Journal American Rhododendron Society, vol. 56, No. 1, 2001, 3 pages.

Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Keith Robinson
(74) *Attorney, Agent, or Firm* — Morrison & Foerster LLP

(57) ABSTRACT

This invention relates to a new and distinct variety of blackberry plant named 'DrisBlackThirteen', particularly characterized by having medium to high productivity, medium-sized, black berries and self-fruitful plants, is disclosed.

2 Drawing Sheets

Genus and species: *Rubus* L. subgenus *Rubus*.
Variety denomination: 'DrisBlackThirteen'.

BACKGROUND OF THE NEW PLANT

The present invention relates to a new and distinct blackberry cultivar designated 'DrisBlackThirteen' and botanically known as *Rubus* L. subgenus *Rubus*. This new blackberry variety was identified in Santa Cruz County, Calif. in December 2009 and originated from a cross between the proprietary female parent blackberry plant 'BP571 (259L4)' (unpatented) and the proprietary male parent blackberry plant 'BP554 (252I5)' (unpatented). The original seedling of the new cultivar was first asexually propagated by tissue culture and root cuttings at a nursery in Santa Cruz County, Calif. in 2009. 'DrisBlackThirteen' was subsequently asexually propagated by tissue culture and root cuttings and underwent further testing at a nursery in Santa Cruz County, Calif. from 2012 to 2014. The present invention has been found to be stable and reproduce true to type through successive asexual propagations.

SUMMARY OF THE INVENTION

The following are the most outstanding and distinguishing characteristics of this new cultivar when grown under normal horticultural practices in Santa Cruz County, Calif.

1. Medium to high productivity;
2. Medium sized, black berries; and
3. Self-fruitful plants.

DESCRIPTION OF THE PHOTOGRAPHS

This new blackberry plant is illustrated by the accompanying photographs which show the plant's canes, flowers, fruit, and leaves. The colors shown are as true as can be reasonably obtained by conventional photographic procedures. The photographs are of plants that are 2 years old.

DESCRIPTION OF THE NEW VARIETY

Figure 1:
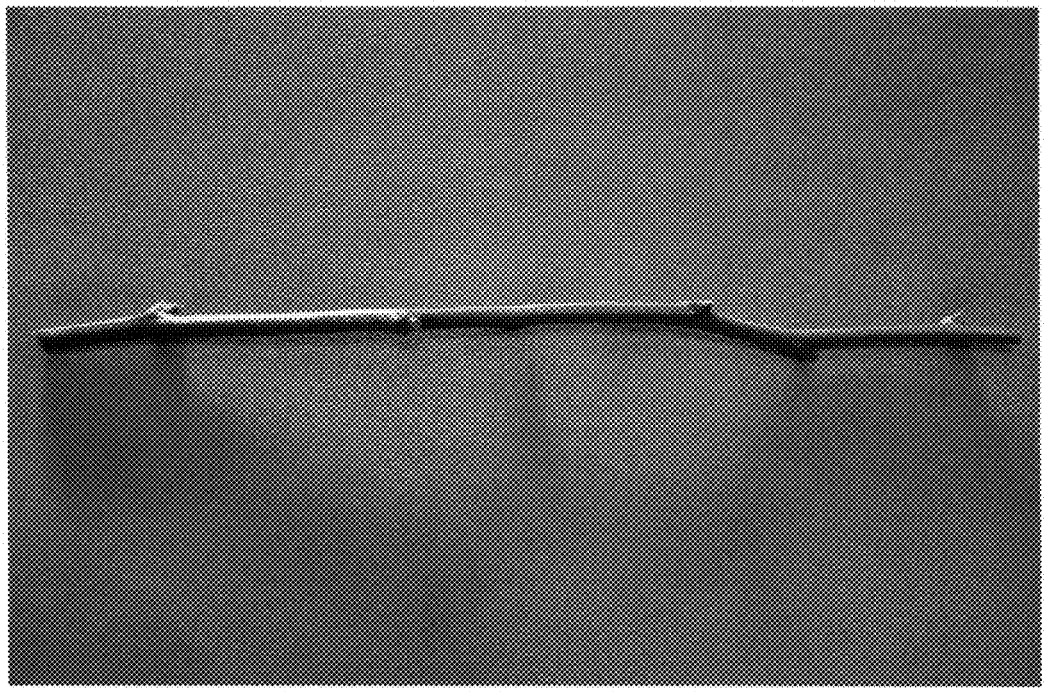
FIG. 1 shows a section of a young cane without spines.
Figure 2:
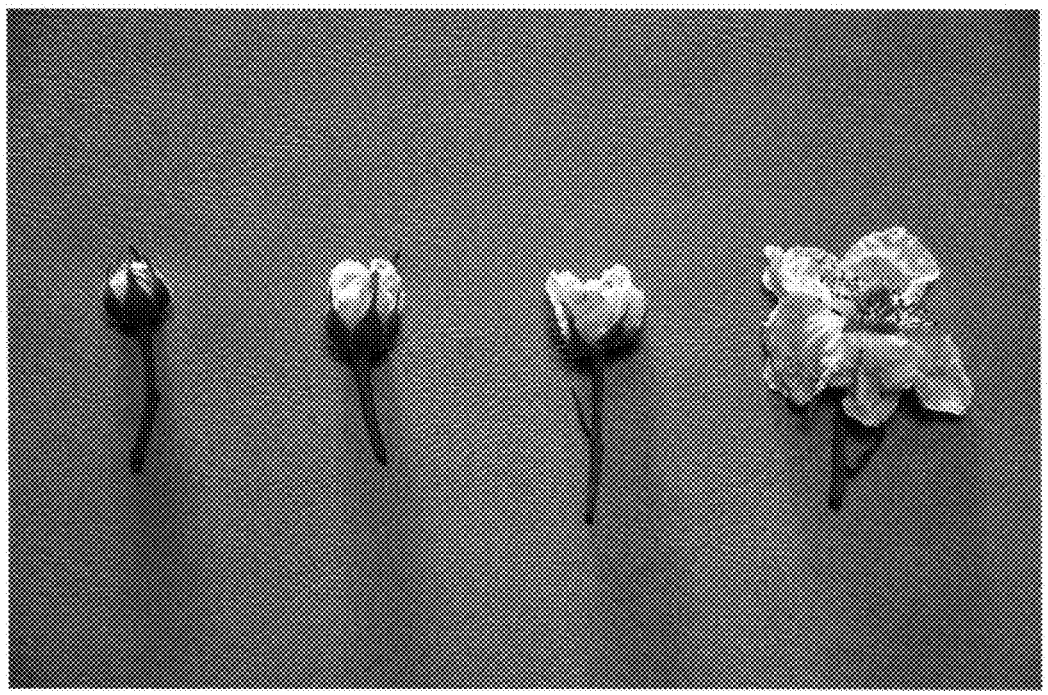
FIG. 2 shows the flowers at various stages.
Figure 3:
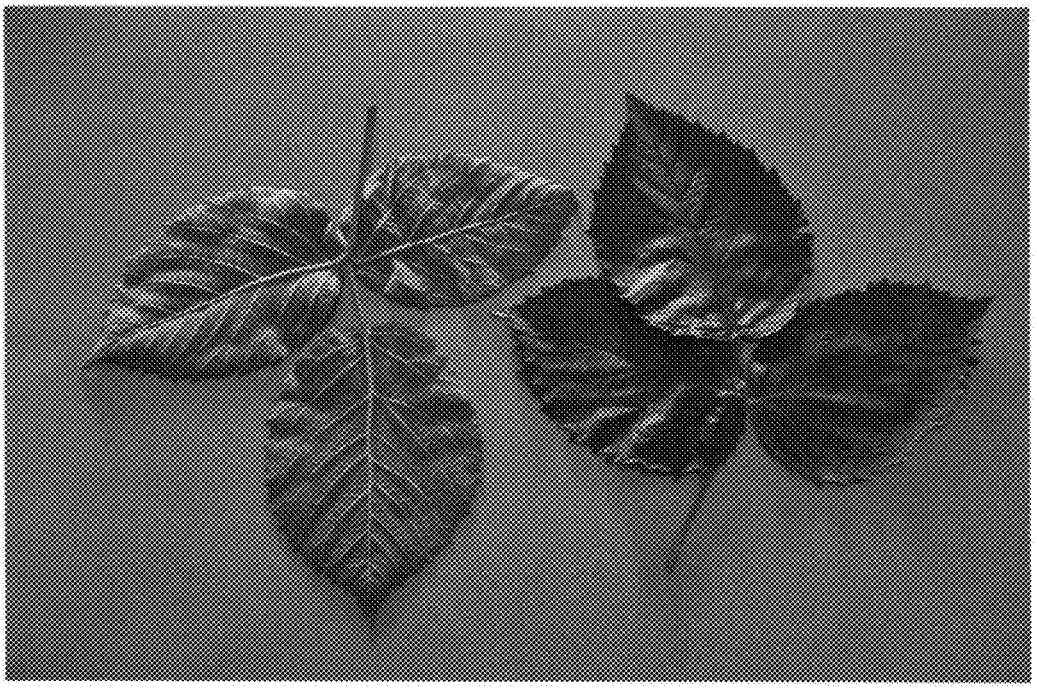
FIG. 3 shows the upper and lower surfaces of the leaves.

The following descriptions of 'DrisBlackThirteen' are based on observations made in Santa Cruz County, Calif. on 2-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackThirteen' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* 2$^{nd}$ edition, by James G. Harris and Melinda Woolf Harris, unless where otherwise defined.

DETAILED BOTANICAL DESCRIPTION

Classification:

*Family*.—Rosaceae.

*Botanical*.—*Rubus* L. subgenus *Rubus*.

*Common name*.—Blackberry.

*Variety name*.—'DrisBlackThirteen'.

Parentage:

*Female parent*.—Proprietary blackberry plant named 'BP571 (259L4)' (unpatented).

*Male parent*.—Proprietary blackberry plant named 'BP554 (252I5)' (unpatented).

Plant:

*Vigor*.—Medium.

*Growth habit*.—Semi-upright.

*Productivity*.—Medium to high.

*Propagation*.—Tissue culture and root cuttings.

*Self-fruitfulness*.—Self-fruitful.

*Time of bud burst*.—February.

Canes:

*Fruiting lateral length* (4$^{th}$ *lateral from tip*).—Medium; 27.3 cm.

*Number of fruit per lateral*.—11.

*Fruiting on current year's cane*.—Present.

*Cane internodal distance*.—5.5 cm.

*Number of new canes during flowering*.—5-6.

*New cane strength* (*observed full-grown shoot after picking*).—Medium to strong.

*Glaucosity observed on full-grown shoot after picking*.—Medium.

*Young shoots*.—Quantity: 5-6. Time of emergence from soil: February. Anthocyanin coloration (during rapid growth): Weak; RHS 181B (Medium greyed-red). Intensity of green color: Medium; RHS 144B (Medium yellow-green).

Dormant cane.—Length: 4-5 ft pruned. Diameter (in central third): 1.0-1.5 cm. Cross section (from mid cane observed at end of first growing season): Angular to grooved. Color: Shade side: RHS 144B (Medium yellow-green). Sun side: RHS 187B (Dark greyed-purple). Number of branches: 15-25. Distribution of branches: Over whole length. Anthocyanin coloration: Medium; RHS 187B (Dark red-purple). Spines: Absent.

Leaves:

*Type*.—Palmate.

*Predominant number of leaflets*.—Five.

*Overlapping or relative position of lateral leaflets*.—Overlapping.

*Color*.—Upper surface: Medium; RHS 144B (Medium yellow-green). Lower surface: Medium; RHS 144B (Medium yellow-green).

*Glossiness of upper side*.—Medium.

*Cross section profile*.—Flat (level with the leaflet blade).

*Leaflets*.—Shape: Ovate. Margin: Doubly serrate. Depth of incisions: 2-5 cm. Type of incision margin: Bi-serrate. Apex: Truncate. Base: Attenuate to Obtuse. Rachis length between terminal leaflet and adjacent lateral leaflet: 49.6 mm.

*Lateral leaflet* (*basal pair*).—Length: 127.7 mm. Width: 89.0 mm. Length/width ratio: 1.4.

*Terminal leaflet*.—Length: Medium to long; 141.4 mm. Width: Medium; 103.9 mm. Length/width ratio: 1.4. Lobing: Absent. Undulation of margin (rippling of margin): Very weak to weak. Blistering between veins (rugosity): Medium. Shape: Ovate to orbicular. Tip: Complex. Base: Obtuse. Margin: Doubly serrate. Cross-section: V-shaped.

*Petiole*.—Length: 21.2 mm. Diameter: 2.4 mm. Pigmentation: Upper surface: Lightly; RHS 144B (Medium yellow-green). Lower surface: Lightly; RHS 144B (Medium yellow-green). Color: RHS 144A (Medium yellow-green).

*Stipule*.—Size: Length of 6.0-15.0 mm and width of 1.0 mm. Orientation: Clasping. Color: RHS 144A (Medium yellow-green).

Inflorescence:

*Flower diameter*.—Medium; 34.57 mm.

*Flower number* (*at* 3$^{rd}$ *node from tip of lateral*).—4.

*Petal*.—Length: 18.00 mm. Width: 15.23 mm. Length/width ratio: 1.2. Color: RHS 69C (Light red-purple).

*Pedicel*.—Length: 18.08 mm. Diameter: 1.56 mm. Color: RHS 143D (Moderate yellow-green).

*Time of beginning of flowering on current year's cane*.—June-August.

Fruit:

*Size*.—Medium.

*Length*.—Short to medium; 32.65 mm.

*Width*.—Medium; 23.43 mm.

*Ratio of length to width*.—Medium; 1.4.

*Weight* (g/*fruit*).—8.7 g.

*Soluble solids* (%) (*in Brix*).—10.5.

*Titratable acidity*.—(% as citric acid): 0.41.

*Seed weight* (g/*seed*).—0.00717.

*Number of drupelets/fruit*.—Medium; 97.17.

*Color*.—Immature: RHS 144B (Medium yellow-green). Maturing: RHS 59C (Medium red-purple). Mature: RHS 203A (Black).

*Firmness*.—Medium to firm.

*Glossiness*.—Weak to medium.

*Shape in longitudinal section*.—Medium ovate.

*Time of ripening on current year's cane*.—July-October.

*Harvest interval*.—Mid-August to mid-November.

*Yield*.—Total yield from plants that were two-years old or older ranged from 7,300 lb/acre to 44,700 lb/acre during a three year period when grown in Watsonville, Calif.

Disease, pest, and stress resistance:

*Verticillium wilt* (*Verticillium spp*.).—Susceptible.

COMPARISON WITH PARENTAL AND COMMERCIAL VARIETIES

'DrisBlackThirteen' differs from the proprietary female parent 'BP571 (259L4)' (unpatented) in that 'DrisBlackThirteen' has larger, firmer fruit with higher Brix and lower titratable acidity than 'BP571 (259L4)'.

'DrisBlackThirteen' differs from the proprietary male parent 'BP554 (252I5)' (unpatented) in that 'DrisBlackThirteen' has much larger, but softer fruit than 'BP554 (252I5)'. Additionally, 'DrisBlackThirteen' is spineless, whereas 'BP554 (252I5)' has spines.

'DrisBlackThirteen' differs from the commercial variety 'DrisBlackTwo' (U.S. Plant Pat. No. 22,002) in that 'DrisBlackThirteen' has medium vigor and medium to high productivity, whereas 'DrisBlackTwo' has high vigor and high productivity. Additionally, 'DrisBlackThirteen' has fruit that is weakly to medium glossy and medium to firm, whereas 'DrisBlackTwo' has fruit that is strongly glossy and firm.

'DrisBlackThirteen' differs from commercial variety 'APF-45' (U.S. Plant Pat. No. 22,449) in that 'DrisBlackThirteen' has medium ovate shaped fruit with lower titratable acidity, whereas 'APF-45' has elongated to blocky to slightly conical shaped fruit with higher titratable acidity.

We claim:

1. A new and distinct variety of blackberry plant named 'DrisBlackThirteen', substantially as illustrated and described herein.

* * * * *